United States Patent [19]

Skurkovich

[11] Patent Number: 4,605,394

[45] Date of Patent: * Aug. 12, 1986

[54] METHODS FOR THE TREATMENT OF PATHOLOGICAL CONDITIONS BY REMOVING INTERFERON FROM THE ORGANISM

[75] Inventor: Simon V. Skurkovich, 261 Congressional La., #709, Rockville, Md. 20852

[73] Assignee: Simon V. Skurkovich, Rockville, Md.

[ * ] Notice: The portion of the term of this patent subsequent to Dec. 7, 1999 has been disclaimed.

[21] Appl. No.: 446,680

[22] Filed: Dec. 3, 1982

[51] Int. Cl.⁴ .................................... A61M 37/00
[52] U.S. Cl. .................................... 604/4; 604/5
[58] Field of Search ............... 128/214 R; 260/112 B; 424/85, 93, 94; 604/4–6

[56] References Cited

U.S. PATENT DOCUMENTS 4,168,261 9/1979 Edy .
4,172,071 10/1979 De Maeyer et al. .
4,223,672 9/1980 Terman et al. .
4,273,703 6/1981 Osther et al. .................... 424/85
4,362,155 12/1982 Skurkovich .................. 128/214 R

OTHER PUBLICATIONS

*Annals of Allergy,* "The Probable Role of Interferon in Allergy"; vol. 35, Dec. 1975; S. V. Skurkovich et al.
*Nature,* "Immunosuppressive Effect of an Anti-Interferon Serum"; Feb. 22, 1974.
*Interferon Scientific Memoranda,* "Interferon Disease, Interferon Syndrome"; Oct. 1980; S. V. Skurkovich.
*Interferon Scientific Memoranda,* "Disturbances of Interferon Synthesis"; Sep. 1982, S. Skurkovich et al.

*Primary Examiner*—C. Fred Rosenbaum
*Assistant Examiner*—Mario A. Costantino

[57] ABSTRACT

Methods are provided for the treatment of pathological conditions connected with the production of other interferons possessing the damaging action on the cell systems of the organism via the continuous removal of interferon from the organism. This is achieved for example by extracorporeal perfusion of the blood of the patient through the substances absorbing, disintegrating, or inactivating biological activity of interferon. The removal of defective interferon is an effective treatment of cancers and leukemias, and immunodeficiencies.

2 Claims, 2 Drawing Figures

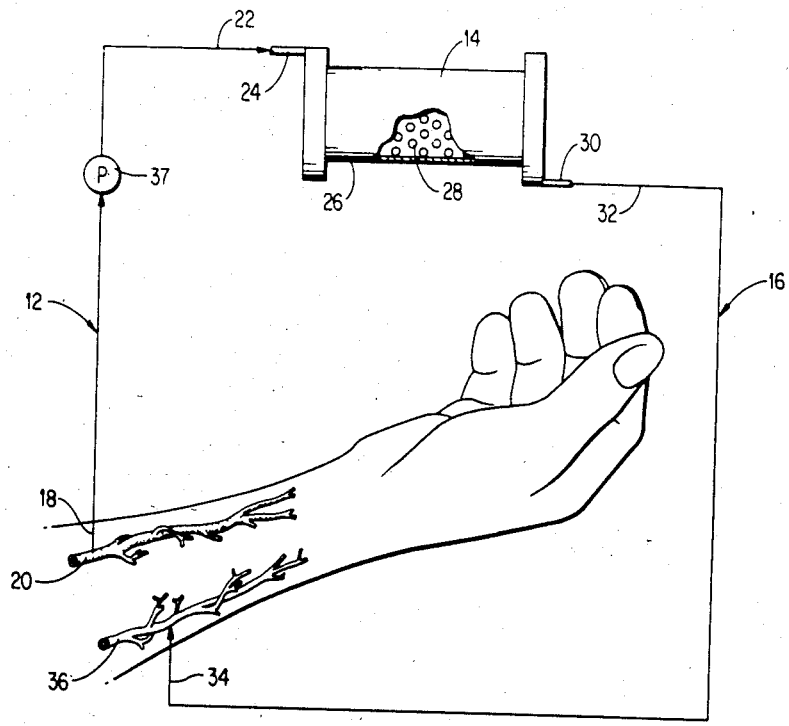
FIG. 1
FIG. 2
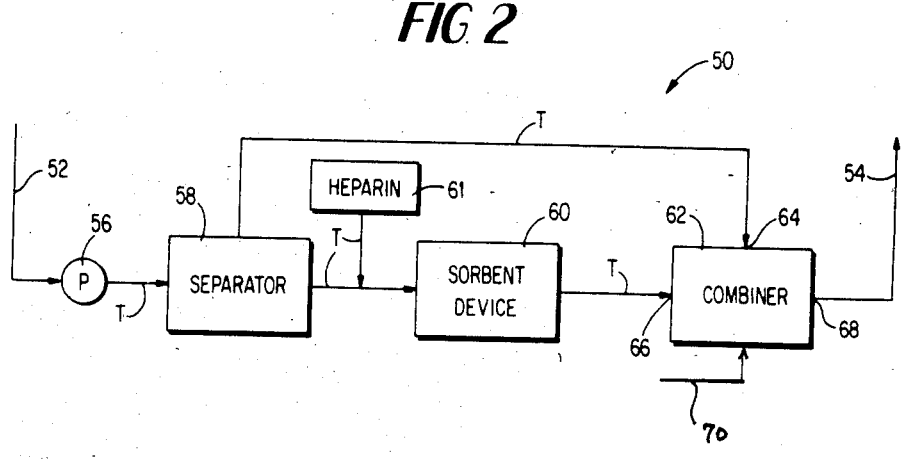

METHODS FOR THE TREATMENT OF PATHOLOGICAL CONDITIONS BY REMOVING INTERFERON FROM THE ORGANISM

FIELD OF THE INVENTION

The present invention relates to the treatment of patients having diseases connected with the production of interferons possessing damaging action on the cells. More particularly, the invention provides a method and apparatus for treating such patients by continuously removing interferon from the blood of a patient being treated.

DESCRIPTION OF THE PRIOR ART

This is a continuation-in-part of U.S. Ser. No. 247,205 filed Mar. 24, 1981, now U.S. Pat. No. 4,362,155 granted Dec. 7, 1982.

In 1975, interferon was discovered in the blood of patients with autoimmune diseases and allergy, and preliminary positive results were obtained in treatment of autoimmune and diseases with anti-interferon immunoglobulin (*Annals of Allergy*, 35:356, December, 1975).

In 1980 and 1982 it was reported that the basis for the development of certain diseases (immune deficiencies, immune suppression in cancer, and others) can be the disturbances of interferon synthesis with the production of defective types of interferon and IFNs possessing damaging action on cells of the organism (Interferon Scientific Memoranda, October 1980, September 1982).

An article entitled "Preparation of Monospecific Immunoglobulin Against Human Leukocytic Interferon" was published in the April 1979, *Bulletin of Experimental Biology and Medicine*. This articles was primarily directed to the preparation of anti-interferon immunoglobulin for its further use as a substance for the treatment of various allergic and autoimmune diseases.

U.S. Pat. No. 4,172,071, the contents of which are herein incorporated by reference, describes a process for the purification of preparations having an interferon type activity. The process described in this patent involves contacting a solution containing products with interferon type activity with an absorbent that permits the interferon to be retained in a selective manner. The interferon is then separated from the absorbent in a subsequent process.

U.S. Pat. No. 4,168,261, entitled "Method For The Purification of Interferon Using Porous Glass Beads", the contents of which are herein incorporated by reference, describes the purification of an aqueous interferon solution by subjecting the solution to chromatography on porous glass beads. The interferon is subsequently eluted from the beads at an acidic pH. Neither of the references is directed to the removal of interferon from blood, plasma, or plasma with leukocytes. Also, neither of the references is directed to the removal of interferon for the purposes of treating diseases related to hyperproduction of interferon or production of interferon possessing damaging action on the cells.

SUMMARY OF THE INVENTION

The present invention provides for methods of treatment of diseases and syndromes connected with hyperproduction of different types of interferon (IFN), and in particular production of inteferons which disinlegrate immune regulation and have a damaging action on the cells of the organism. These methods include the use of different agents binding, disintegrating, or blocking biological activity of selected interferons and comprise, e.g., antibodies, enzymes, and or other substances. These agents can be administered into the organism, or used in the apparatus for extracorporeal perfusion where the blood containing IFN is passed through these substances which are immobilized, thus clearing the blood from interferon.

These methods can be used for the treatment of immune deficiencies, negative features of aging immuno suppression in cancers and leukemias and other conditions connected with damaging action of IFNs. It is preferable to administer normal IFNs after the removal of IFNs which have a damaging action on cells.

The invention, and its objects and advantages, will become more apparent in the detailed description of the preferred embodiments hereinafter presented.

BRIEF DESCRIPTION OF THE DRAWINGS

In the detailed description of the preferred embodiments of the invention hereinafter presented, reference is made to the accompanying drawings, in which:

FIG. 1 is a schematic illustration of one embodiment apparatus provided by the present invention; and FIG. 2 is a schematic block diagram of another embodiment of the present invention.

PREFERRED EMBODIMENTS OF THE INVENTION

The present invention provides for methods of treatment of diseases and syndromes connected with production of interferons which disintegrate immune regulations and possess damaging action on the cells of the organism of a patient. Thus, antibodies, enzymes or similarly reacting agents are used for binding, disintegrating or blocking the biological activity of these interferons. The invention preferably uses an apparatus for extracorporeal perfusion where the blood containing interferon is passed through an external reaction chamber containing the above agents and thus the interferon is cleared from the blood. Treatment may also be achieved by the administration of the agents into the organism of the patient to neutralize or remove the damaging effect of the interferon.

The present invention provides for methods of treatment of, immune deficiencies, negative features of aging immuno suppression in cancers and leukemias, and other conditions connected with damaging action of IFN.

The invention utilizes apparatus for removing from or disintegrating, or blocking biological activity of interferon in the organism, and for returning blood having a reduced amount or free from interferon to the patient. Normal interferon may be introduced to the patient after the completion of the clearance process. Hereinafter, the terminology "clearance from interferon" will be used to describe blood that has either a reduced level of interferon or is completely free from interferon by absorption, disintegration, inactivation or suppression of the biological activity of interferon. The method is achieved by apparatus preferably in a closed system in which all of the parts are in fluid communication. During the treatment of a patient, the process of clearance from interferon from the blood is continuous. With this embodiment, the apparatus clears interferon from the whole blood of the patient.

In another embodiment of the invention, a method and apparatus are provided in which interferon is cleared from plasma. Alternatively, the interferon is cleared from plasma containing leukocytes. In either of these cases, it is necessary to pass the whole blood through a blood separator before clearance. Such separator can be a filter or a plasma/cell separator of the type manufactured by American Instrument Co. of Silver Spring, Md. With the embodiment, blood from the patient is first pumped to the separator. The separator separates the blood into plasma (or plasma with leukocytes) and blood cells. Then plasma, or plasma with leukocytes, is pumped from the separator to the clearance system. After clearance of interferon, the plasma or plasma with leukocytes, is rejoined with the blood cells or formed elements of the blood and returned to the patient.

Suitable techniques for purifying interferon are described in the aforementioned U.S. Pat. Nos. 4,168,261 and 4,172,071. These techniques are also usable with the present invention for removing interferon. It should be appreciated that the techniques in these references will require minor modifications when used in the present invention.

For the clearance from interferon the present invention uses anti-interferon antibodies, albumen, and other substances capable of absorbing, disintegrating, inactivating or suppressing the biological activity of interferon. A suitable solid support for these substances may be the Sepharose as described in U.S. Pat. No. 4,172,071.

Blood cleared from interferons which have a damaging action on cells is returned to the patient. It is expedient to administer normal interferons after the removal of abnormal interferons described above.

The following description will be directed in particular to elements forming part of, or cooperating more directly with, the present invention. Elements not specifically shown or described herein are understood to be selectable from those known in the art.

Referring now to the drawings, and to FIG. 1 in particular, one embodiment of an apparatus for treatment of blood to clear interferon is illustrated. The apparatus, which is generally designated 10, comprises an inlet tube 12, means 14 for clearing interferon from blood, and an outlet tube 16. The inlet tube 12 has an inlet end 18 connected to a cannula (not shown) inserted into an artery or blood vessel 20 of a patient. The outlet end 22 of the inlet tube 12 is connected to the inlet 24 of a housing 26 containing a plurality of porous glass beads 28, such as those described in U.S. Pat. No. 4,168,261. The outlet 30 of the housing 26 is connected to an end 32 of the outlet tube 16. The other (outlet) end 34 of tube 16 is connected to a cannula (not shown) inserted into a vein 36 of the patient. Preferably, a pump 36 is included in the apparatus 10. The inlet tube 12 provides means for removing whole blood from a patient, and the outlet tube 16 provides means for returning the blood to the patient. As clearly illustrated in FIG. 1, the tubes 12 and 16 and the means 14 are in continuous fluid communication with each other.

In operation, the cannula connected to the inlet 18 is inserted into the blood vessel of the patient, and the cannula connected to the outlet 34 is inserted into a vein. When a pump is used, the pump is then actuated to pump blood from the patient through the housing 26 so that the beads 28 can remove interferon from the blood. Preferably, all of the interferon is removed from the blood. Blood free from interferon is then returned through the outlet tube 16 into the vein of the patient.

The method used with this embodiment of the invention provides a continuous process for treatment of conditions connected with the damaging action of IFN. The process involves removing blood from a patient, passing the removed blood through means for clearance of the blood from IFN, and returning the blood, which is free from interferon, to the patient.

Referring now to FIG. 2, another embodiment of an apparatus according to the present invention, generally designated 50, is illustrated. The apparatus 50 includes an inlet tube, generally designated 52, and an outlet tube, generally designated 54. The outlet tube 52 is similar to the inlet tube 12, and the outlet tube 54 is similar to the outlet tube 16 of the embodiment illustrated in FIG. 1. A pump 56 is provided to pump blood from the patient into a separator 58. A suitable separator is a plasma filter of the type described in British Pat. No. 1,562,546. Other suitable methods of plasmapheresis, such as centrifugation, also are usable to separate plasma or plasma with leukocytes from the whole blood. The plasma, or plasma with leukocytes, is fed from the separator 58 to a sorbent containing device 60 charged with the aforementioned anti-interferon antibodies. Such device can be the means 14 for removing interferon described in connection with FIG. 1, in general, a device using a process of the type described in U.S. Pat. No. 4,172,071, or any other suitable method using a capacious sorbent for interferon carried by a solid support. The plasma, or plasma with leukocytes, after passing through sorbent within the device 60, rejoins the formed elements of blood removed from the whole blood by the separator 58. A combiner 62 is illustrated for providing the mixing function. Such combiner need be no more complex than a mixing valve having one inlet 64 connected to the separator 58 and a second inlet 66 connected to the device 60. The outlet 68 of the valve is connected to the outlet tube 54. A device 61 for adding heparin to the plasma, or plasma with leukocytes, is positionable between the separator 58 and the device 60. Sections of tubing T interconnect the pump 56, the separator 58, the device 60, the device 61, and the combiner 64, as illustrated in FIG. 2. Thus, the various components of the apparatus 50 are in fluid communication with each other.

The method of clearing blood for treating diseases and conditions connected with damaging action of IFN utilizing the apparatus of FIG. 2 involves the connecting of the inlet and outlet tubes to blood vessel and a vein, respectively, of a patient to be treated; pumping the whole blood of the patient to a separator; separating plasma, or plasma with leukocytes, from blood cells within the separator; passing the plasma, or plasma with leukocytes, through a device for clearing interferon; combining the plasma, or plasma with leukocytes, after clearance of interferon, with the previously removed blood cells; and returning the combined blood to the patient.

In a modification of this embodiment, the separator device separates the blood into plasma (or plasma with leukocytes), and other blood cells. The plasma (or plasma with leukocytes) is processed as previously described.

In another modification, the device 60 utilizes a combined sorbent having a first component for absorbing interferon from the plasma or plasma with leukocytes and a second component that selectively absorbs blocking antibodies in cases of cancers and leukemias, from the plasma or plasma with leukocytes being treated.

The particular component is a function of the disease or condition being treated. By utilizing a combined sorbent, the effectiveness of the invention is enhanced.

SPECIFIC EXAMPLES

The present invention includes the following embodiments:

A.

Diseases are treated by the steps of selectively removing blood from the patient, processing the blood of the patient with the means to clear it from interferon, and returning the blood to the patient, while keeping the blood flow path in continuous fluid communication.

B.

The method of treatment of diseases is also carried out by including the step of blocking biological activity of interferon with an interferon clearing agent.

C.

Diseases are also treated by including the steps of separating plasma from the blood residue and processing only the plasma to clear it of interferon, combining the so processed plasma with the blood residue, and returning the combined blood to the patient.

D.

The method of treatment of diseases also includes the step of separating plasma with leukocytes from whole blood, and processing plasma with leukocytes to clear it of interferon, combining the so processed plasma with leukocytes with the blood residue, and returning the combined blood to the patient.

E.

Also included is the step of administering normal interferon after completion of the clearance of interferon process and returning blood to the patient.

F.

The treatment of the present invention includes the step of administering an interferon clearing agent to the organism of the patient to clear interferon from the bloodstream.

G.

Also included is the step of removing blocking antibodies from the blood of cancer patients.

Those novel features believed descriptive of the spirit and nature of the invention are defined with particularity in the claims.

We claim:

1. In a method of treating diseases comprising the step of selectively clearing the blood of a patient from interferon using an apparatus having, in continuous fluid communication, an inlet tube, absorbing means for absorbing and thereby removing interferon from the whole blood, and an outlet tube, said method comprising:

connecting the inlet tube of said apparatus to a blood vessel of a patient and connecting the outlet tube of said apparatus to a vein of the patient;

removing blood from the blood vessel of the patient;

passing the removed blood through the absorbing means for absorbing interferon to thereby reduce the amount of interferon in the blood; and returning the blood to the vein of the patient, the improvement comprising:

administering normal interferon after completion of the clearance of interferon process and returning the blood containing normal interferon to the patient.

2. In a method of treating diseases comprising the step of selectively clearing the blood of a patient from interferon using an apparatus having, in continuous fluid communication, an inlet tube, absorbing means for absorbing and thereby removing interferon from the whole blood, and an outlet tube, said method comprising:

connecting the inlet tube of said apparatus to a blood vessel of a patient and connecting the outlet tube of said apparatus to a vein of the patient;

removing blood from the blood vessel of the patient;

separating the removed blood into blood cells and plasma:

passing the plasma through the absorbing means for absorbing interferon to thereby reduce the level of interferon within the plasma;

combining the plasma having a reduced level of interferon with the blood cells previously removed from the blood; and returning the combined blood cells and plasma to the vein of the patient;

the improvement comprising:

administering normal interferon after completion of the clearance of interferon process and returning the blood containing normal interferon to the patient.

* * * * *

UNITED STATES PATENT AND TRADEMARK OFFICE
CERTIFICATE OF CORRECTION

PATENT NO. : 4,605,394
DATED : August 12, 1986
INVENTOR(S) : Simon V. SKURKOVICH It is certified that error appears in the above-identified patent and that said Letters Patent is hereby corrected as shown below:

The title page, the ABSTRACT should be corrected to read:

-- Methods are provided for the treatment of pathological conditions connected with the production of other interferons possessing the damaging action on the cell systems of the organism via the continuous removal of interferon from the organism. This is achieved for example by extracorporeal perfusion of the blood of the patient through the substances absorbing, disintegrating, or inactivating biological activity of interferon. --

Signed and Sealed this

Ninth Day of December, 1986

Attest:

DONALD J. QUIGG

Attesting Officer

Commissioner of Patents and Trademarks